United States Patent [19]

Barnes et al.

[11] Patent Number: 4,599,095
[45] Date of Patent: Jul. 8, 1986

[54] THIN BED SORPTION/DESORPTION APPARATUS AND METHOD FOR MAKING THE SAME

[75] Inventors: David A. Barnes, Seminole; Eugene L. Szonntagh, Largo, both of Fla.

[73] Assignee: Honeywell Inc., Minneapolis, Minn.

[21] Appl. No.: 663,109

[22] Filed: Oct. 22, 1984

[51] Int. Cl.⁴ .................... B01D 35/18; B01D 53/04
[52] U.S. Cl. ..................... 55/208; 55/269; 55/387; 219/548; 338/212
[58] Field of Search ............. 55/208, 267, 269, 387; 219/240, 494, 544, 548, 549; 338/34, 35, 212, 254, 255

[56] References Cited

U.S. PATENT DOCUMENTS

| | | | |
|---|---|---|---|
| 2,067,920 | 1/1937 | Heuser | 55/208 X |
| 2,471,442 | 5/1949 | Morf | 55/208 |
| 2,596,979 | 5/1952 | Case | 55/208 |
| 2,989,383 | 6/1961 | Miller | 55/267 X |
| 3,296,773 | 1/1967 | Hemstreet | 55/269 X |
| 3,309,844 | 3/1967 | Hemstreet et al. | 55/269 X |
| 3,338,034 | 8/1967 | Hemstreet | 55/269 |
| 3,486,002 | 12/1969 | Eno et al. | 55/208 X |
| 3,584,198 | 6/1971 | Doi et al. | 219/544 X |
| 3,627,988 | 12/1971 | Romaniec | 219/544 X |
| 3,693,323 | 9/1972 | Gant | 55/208 X |
| 3,697,728 | 10/1972 | Stirzenbecher | 219/544 X |
| 4,055,526 | 10/1977 | Kiyokawa et al. | 219/548 X |
| 4,060,710 | 11/1977 | Reuter et al. | 219/548 |
| 4,242,573 | 12/1980 | Batliwalla | 219/544 X |
| 4,325,220 | 4/1982 | McFarlin | 55/269 X |
| 4,501,951 | 2/1985 | Benin et al. | 219/544 X |

FOREIGN PATENT DOCUMENTS 1341729 12/1973 United Kingdom .................. 55/269

OTHER PUBLICATIONS

Minco Products, Inc., Bulletin TF-5 Thermofoil Heat Fusers, 4 pages, 3-20-75.

Primary Examiner—Robert Spitzer
Attorney, Agent, or Firm—Mitchell J. Halista; Trevor B. Joike

[57] ABSTRACT

A thin bed sorption/desorption apparatus includes a heater element laminated within a high temperature chemically inert polymer with an adhesive on the outside of the laminate being used to attach a thin film of small particle size sorptive material. Various embodiments of the apparatus are each arranged to provide a flow of a sample to be analyzed across the surface of the sorptive material. The method for making the thin bed sorption/desorption apparatus includes the steps of encapsulating a thin-film heater element in a laminated structure of a polyimide which is a high temperature, chemically inert polymer. The outside surface of the laminate is coated with a polyimide adhesive which is diluted with dimethyl formamide. The sorptive material in the form of a powder having a maximum particle size of 100 mesh is applied to the wet adhesive. Subsequently, the coated structure is heat cured at approximately 220° C. for a period of approximately 30 minutes until the adhesive is dry and the sorptive material layer is fixed to the laminate.

12 Claims, 4 Drawing Figures

THIN BED SORPTION/DESORPTION APPARATUS AND METHOD FOR MAKING THE SAME

BACKGROUND OF THE INVENTION

The present invention relates to gas analyzers. More specifically, the present invention is directed to a sorption/desorption apparatus for a gas analyzer.

DESCRIPTION OF THE PRIOR ART

Conventional sorption/desorption devices used in gas analysis apparatus have employed packed columns of sorptive material through which gas samples are directed while selected constituents are adsorbed by the sorptive material. Those columns have had varying lengths and are heated by external heaters to desorb the adsorbed constituents of the gas sample. Such sorption columns have several serious disadvantages including a significant flow restriction to the sample gas and an inefficient desorption mode as a result of a slow heat transfer to the sorptive material and a diffused peak of the desorbed constituents. Accordingly, in order to improve the operation of the gas analysis apparatus, the present invention provides a sorption/desorption device having a minimal flow restriction to the sample gas and a rapid heat transfer to the sorptive material to produce a well-defined desorbed constituent peak.

SUMMARY OF THE INVENTION

An object of the present invention is to provide an improved method for making a sorption/desorption apparatus.

Another object of the present invention is to provide an improved sorption/desorption bed apparatus.

In accomplishing these and other objects, there has been provided, in accordance with the present invention, a method for making a sorption/desorption bed including the steps of laminating a thin film heater element within a chemically inert and high temperature material, applying an adhesive to the outside surface of the laminate, coating the adhesive with a thin layer of a fine sorptive material powder and drying the adhesive to fix the powder on the laminate. A sorption/desorption bed utilizing the method of the present invention includes a thin film heater element, a high temperature chemically inert laminate housing the heater element, an adhesive on an outside surface of the laminate and a thin film of a small particle size sorptive material affixed to the laminate by the adhesive.

BRIEF DESCRIPTION OF THE DRAWINGS

A better understanding of the present invention may be had when the following detailed description is read in connection with the accompanying drawings, in which.

DESCRIPTION OF THE PREFERRED EMBODIMENT

Detailed Description

Figure 1:
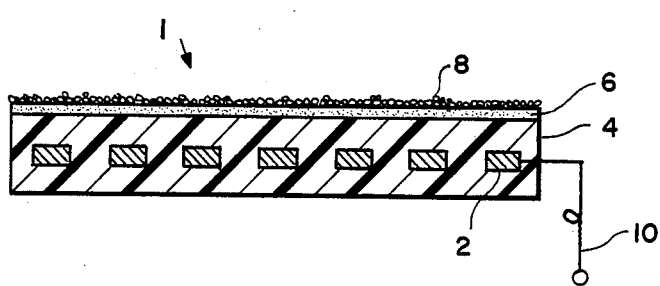
FIG. 1 is a cross-sectional illustration of a sorption/desorption bed made according to the method of the present invention.

The sorption/desorption bed 1 as shown in FIG. 1 includes a thin film labrynth heater element 2 known as "Thermofoil" as manufactured by Minco, Inc., Minneapolis, Minn. The heater element 2 is laminated within a polyimide envelope 4, which is preferably a high temperature, chemically inert polymer such as Kapton manufactured by The DUPONT CO., Wilmington, Del. The total thickness of the heater element 2 is approximately 6.5 mil. The heater 4 laminate (approx. 6.5 mil total thickness) is subsequently coated with a polyimide adhesive 6 diluted by dimethyl formamide by dipping the laminate into the diluted adhesive. A powder of a sorptive material 8 such as Carbopack, a graphitized carbon black manufactured by Supelco Inc., Bellefonte, PA, is sprinkled on the adhesive layer 6 while the adhesive is still wet to form a a thin coating on the surface of the adhesive. The sorptive material 8 is a fine powder having a maximum 1 particle size of 100 mesh. Subsequently, the coated bed is heat-cured at approximately 220° C. for up to 30 minutes to thoroughly dry the adhesive and fix the powder to the laminate 4. The heater element 2 is provided with electrical connections at its respective ends extending out of the sorption bed 1, e.g., the electrical connection 10 shown in FIG. 1.

The resulting structure has the sorptive material 8 in close thermal contact with the heater film 2, a large surface area of the sorptive material 8 and a small thermal mass for quick heating and cooling. A sorption/desorption bed 1 using the aforesaid structure and having a surface area of approximately one square inch will require only approximately 0.2 watts of power to energize the heater element 2. Accordingly, the heater element 2 may be energized for flash heating of the sorptive material 8 to produce a desorption of the sample retained therein by a capacitive discharge through the heater element 2 to produce a heating cycle of a fraction of a second, e.g., 0.1 second.

Figure 2:
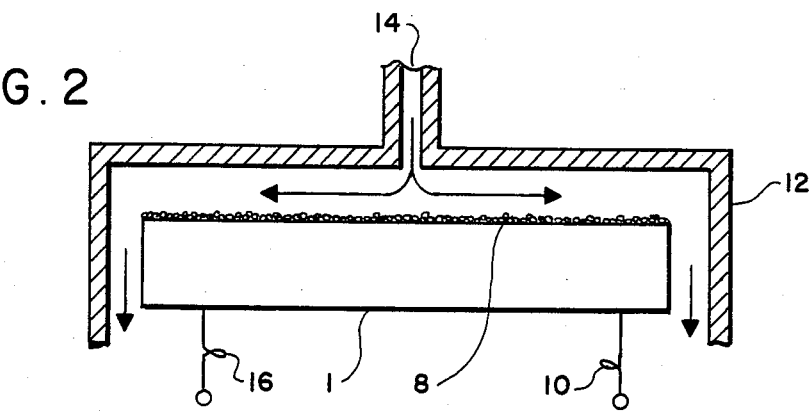
FIG. 2 is an example of an embodiment of the sorption/desorption bed shown in FIG. 1 in an operative configuration.

In FIG. 2, there is shown an application of an embodiment of the sorption/desorption bed 1 made in accordance with the method of the present invention in a first operative configuration. In this arrangement, the sorption bed 1 is located within an outer shell or housing 12 for guiding the flow of a sample gas to be adsorbed across the sorptive material 8 on the bed 1 by having a sample inlet 14 in the housing 12 located coaxially with the flat sorption bed 1 while the inner wall of the housing 12 is spaced from the surface of the sorption bed 1 to provide a small volume for the flow of the sample gas across the bed 1. The close spacing of the housing 12 to the sorption/desorption bed 8 enables the use of very small flow volumes (in the order of magnitude 100 microliters or less) resulting in large sensitivity enhancement. The sample gas ultimately flows around the ends of the sorption bed 12 to an outlet (not shown) from the housing 12. A second electrical connector 16 is provided for completing the electrical circuit through the labrynth heater element 2 from the aforesaid first electrical connector 10.

Figure 3:
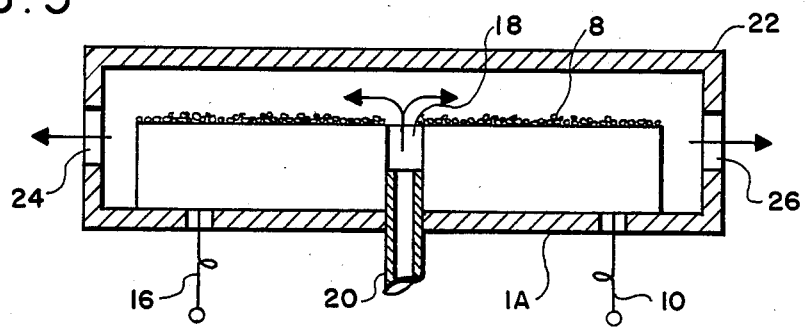
FIG. 3 is a second embodiment of a sorption/desorption bed using the structure shown in FIG. 2 in a second operative configuration and FIG. 4 is a cross-sectional illustration of a sorption/desorption bed using the structure shown in FIG. 1 in a third operative configuration.

In FIG. 3, there is shown a sorption bed 1A in a second operative configuration. The sorption bed 1A shown in FIG. 3 includes a coaxial opening 18 therethrough. A sample inlet pipe 20 extends through a housing 22 encasing and spaced from the bed 1A. An end of the pipe 20 is located within the central bed opening 18. A first exit port 24 at one end of a housing 22 and a second exit port 26 at the other end of the housing 22 provide outlets for a sample gas after the sample gas is admitted into pipe 20 and is guided across the surface of the sorptive material 8 by housing 22. As in the case of the configuration shown in FIG. 2, the housing 22 is closely spaced from the bed 1A to produce a small flow volume.

Figure 4:
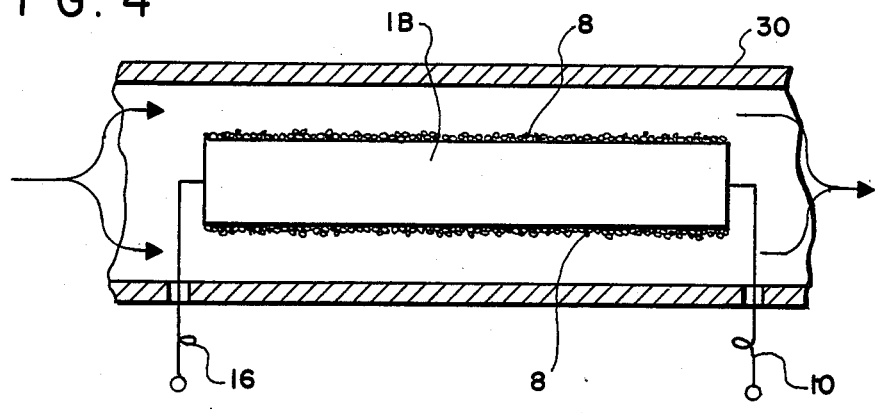

In FIG. 4, there is shown a sorption bed 1B in a third operative configuration including a coating of the sorptive material 8 on both sides of the sorptive bed 1B. A housing 30, e.g., a pipeline, is closely spaced from the bed 1B and is arranged to guide a sample gas around both sides of the sorption bed 1B across the sorption layer 8. It should be noted that bed 1B may be flat, cylindrical, etc.

Accordingly, it may be seen, that there has been provided a method for making an improved sorption/desorption bed and a sorption/desorption bed made in accordance with this method.

The embodiments of the invention in which an exclusive property or privilege is claimed are defined as follows:

1. A method for making a sorption/desorption bed including the steps of laminating a thin film heater element within a high temperature, chemically inert material, coating an outside surface of the laminate with an adhesive, covering the adhesive with a thin layer of a small particle sorptive material and heating the structure to dry the adhesive to fix the sorptive material to the laminate to provide an external sorptive coating for the bed in close thermal contact with the thin film heater element so that there is a large surface area of the sorptive material and a small thermal mass for quick heating and cooling.

2. A method as set forth in claim 1 wherein the sorptive material is comprised of particles of a size smaller than 100 mesh.

3. A method as set forth in claim 1 wherein the heating of the bed is performed at a temperature of approximately 220° C. for approximately 30 minutes.

4. A sorption/desorption bed comprising
a thin film heater element,
a chemically inert, high temperature laminate encapsulating the heater element,
a high temperature adhesive on an outside surface of said laminate and
thin coating of a sorptive material on an outside surface of said adhesive to provide a sorptive outside surface for the bed in close thermal contact with the thin film heater element so that there is a large surface area of the sorptive material and a small thermal mass for quick heating and cooling.

5. A bed as set forth in claim 4 wherein said sorptive material coating has a thickness of approximately 0.1 mil.

6. A bed as set forth in claim 5 wherein said material coating is comprised of particles having a size smaller than 100 mesh.

7. A bed as set forth in claim 4 and further includes a housing enclosing the bed and having a flow inlet and a flow outlet while being closely spaced from said bed to provide a small flow volume across said bed.

8. A bed as set forth in claim 7 wherein said laminate has a cylindrical configuration and said housing is a pipeline having a circular cross-section.

9. A bed as set forth in claim 7 wherein said housing has an inlet coaxial with said outlet.

10. A bed as set forth in claim 7 wherein said inlet extends through said laminate and said outlet is located adjacent to a periphery of said laminate.

11. A bed as set forth in claim 4 wherein said laminate has a flat configuration.

12. A bed as set forth in claim 4 wherein said laminate has a cylindrical configuration.

* * * * *